(12) United States Patent
Chen et al.

(10) Patent No.: US 6,852,733 B2
(45) Date of Patent: Feb. 8, 2005

(54) SODIUM-HYDROGEN EXCHANGER TYPE 1 INHIBITOR

(75) Inventors: Weichao G. Chen, Old Saybrook, CT (US); Eric D. Cox, Groton, CT (US); Angel Guzman-Perez, Stonington, CT (US)

(73) Assignee: Pfizer Inc., Groton, CT (US)

( * ) Notice: Subject to any disclaimer, the term of this patent is extended or adjusted under 35 U.S.C. 154(b) by 0 days.

(21) Appl. No.: 09/836,035

(22) Filed: Apr. 17, 2001

(65) Prior Publication Data

US 2001/0051634 A1 Dec. 13, 2001

Related U.S. Application Data

(60) Provisional application No. 60/200,432, filed on Apr. 28, 2000.

(51) Int. Cl.[7] ............... A61K 31/4709; A61K 31/4704; C07D 401/04; C07D 215/227
(52) U.S. Cl. .................. 514/312; 546/157; 546/167; 546/153; 514/314
(58) Field of Search ................. 546/157, 167, 546/153; 514/314, 312

(56) References Cited

U.S. PATENT DOCUMENTS 6,492,401 B1 * 12/2002 Hamenaka .................. 514/359

FOREIGN PATENT DOCUMENTS

| EP | 1101763 | 5/2001 |
| JP | 9826803 | 6/1998 |
| WO | WO 9827061 | 6/1998 |
| WO | WO 9935137 | 7/1999 |
| WO | WO 9943663 | 9/1999 |

OTHER PUBLICATIONS

Principles of Pharmacology. Basic Concepts & Clinical Applications. (1995) Edited by Munson et al. Chapman & Hall. pp. 52–56.*

Beedham et al. Drug Metabolism and Disposition. (Nov.–Dec. 1992) 20(6), 889–95.*

Beedham C et al. Drug Metablism and Disposition. 1992, 20(6), 889–895.*

W.J. Ehlhardt et al., Drug Metab. & Dispo., 26, No, 1, 42–51 (1998).

* cited by examiner

*Primary Examiner*—Evelyn Mei Huang
(74) *Attorney, Agent, or Firm*—Peter C. Richardson; Charles Ashbrook; John H. Engelmann

(57) ABSTRACT

NHE-1 inhibitor, methods of using the NHE-1 inhibitor and pharmaceutical compositions containing the NHE-1 inhibitor. The NHE-1 inhibitor is useful for the reduction of tissue damage resulting from tissue ischemia.

30 Claims, No Drawings

SODIUM-HYDROGEN EXCHANGER TYPE 1 INHIBITOR

This application is filed claiming priority from co-pending Provisional Application No. 60/200,432 filed Apr. 28, 2000.

BACKGROUND OF INVENTION

This invention relates to a sodium-hydrogen exchanger type 1 (NHE-1) inhibitor.

Myocardial ischemic injury can occur in out-patient as well as in perioperative settings and can lead to the development of sudden death, myocardial infarction or congestive heart failure. There is an unmet medical need to prevent or minimize myocardial ischemic injury, particularly perioperative myocardial infarction. Such a therapy is anticipated to be life-saving and can reduce hospitalizations, enhance quality of life and reduce overall health care costs of high risk patients.

Pharmacological cardioprotection would reduce the incidence and progression of myocardial infarction and dysfunction occurring in these surgical settings (perioperatively). In addition to reducing myocardial damage and improving post-ischemic myocardial function in patients with ischemic heart disease, cardioprotection would also decrease the incidence of cardiac morbidity and mortality due to myocardial infarction-and dysfunction in patients "at risk" (such as greater than 65 years, exercise intolerant, coronary artery disease, diabetes mellitus, hypertension) that require non-cardiac surgery.

The mechanism(s) responsible for the myocardial injury observed after ischemia and reperfusion is not fully understood.

A variety of publications have disclosed the use of guanidine derivatives as useful for the treatment of, for example, arrhythmias.

A recent published patent application, PCT/IB99/00206 published as WO 99/43663 on Sep. 2, 1999, the disclosure of which is hereby incorporated by reference, discloses a variety of NHE-1 inhibitors including [5-cyclopropyl-1-(quinolin-5-yl)-1H-pyrazole-4-carbonyl]guanidine. The publication further states that "preferred salts of the immediately preceding compound are the mono- or di-mesylate salts." One group of preferred compounds, which include hydroxyquinoline compounds, is described in claim 102 of the published application. Of course, some of these hydroxyquinoline compounds can exist in several tautomeric forms such as the quinolone form as described in that patent application. In addition, commonly assigned U.S. provisional application Ser. No. 60/162,374 was filed on Oct. 29, 1999 and is directed to crystal forms of the above described NHE-1 inhibitor.

PCT/JP97/04650 application published on Jun. 25, 1998 discloses N-[(substituted five-membered heteroaryl)]guanidine compounds to be useful as inhibitors of $Na^+/H^+$ exchange and consequently effective for the treatment of various diseases such as hypertension, arrhythmia, angina pectoris, myocardial infarct, arteriosclerosis, and complications of diabetes.

Thus, there is clearly a need and a continuing search in this field of art for compounds for the treatment of perioperative myocardial ischemia.

SUMMARY OF THE INVENTION

This invention is directed to a compound of Formula I

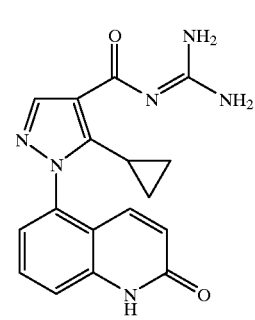

Formula I a prodrug thereof, or a pharmaceutically acceptable salt of said compound or of said prodrug, with the proviso that [5-cyclopropyl-1-(quinolin-5-yl)-1H-pyrazole-4-carbonyl]guanidine is not included.

As used herein the phrase "a prodrug thereof, or a pharmaceutically acceptable salt of said compound or of said prodrug" includes the proviso that [5-cyclopropyl-1-(quinolin-5-yl)-1H-pyrazole-4-carbonyl]guanidine is not included.

This invention is also directed to substantially pure [5-cyclopropyl-1-(2-quinolon-5-yl)-1H-pyrazole-4-carbonyl]guanidine, or a pharmaceutically acceptable salt of said compound.

Alternatively, the above compound is named [5-cyclopropyl-1-(2-quinolon-5-yl)-1H-pyrazole-4-carbonyl]guanidine. A preferred salt is the hydrochloride salt, and most preferably, the monohydrochloride salt.

Another aspect of this invention is a method of treating a mammal (e.g., human) having a disease or condition mediated by NHE-1 by administering a therapeutically effective amount of the Formula I compound, a prodrug thereof, or a pharmaceutically acceptable salt of said compound or of said prodrug to the mammal.

Another aspect of this invention is directed to a method of reducing tissue damage (e.g., substantially preventing tissue damage, inducing tissue protection) resulting from ischemia comprising administering to a mammal (e.g., a female or male human) in need of such treatment a therapeutically effective amount of the Formula I compound, a prodrug thereof, or a pharmaceutically acceptable salt of said compound or of said prodrug.

Preferred ischemic tissues taken individually or as a group are cardiac, brain, liver, kidney, lung, gut, skeletal muscle, spleen, pancreas, nerve, spinal cord, retina tissue, the vasculature, or intestinal tissue.

An especially preferred ischemic tissue is cardiac tissue.

It is especially preferred that the Formula I compound, a prodrug thereof, or a pharmaceutically acceptable salt of said compound or of said prodrug is administered to prevent perioperative myocardial ischemic injury.

Preferably, the Formula I compound, a prodrug thereof, or a pharmaceutically acceptable salt of said compound or of said prodrug is administered prophylactically.

The ischemic damage may occur during organ transplantation either to the organ or the patient.

Preferably, the Formula I compound, a prodrug thereof, or a pharmaceutically acceptable salt of said compound or of said prodrug is administered prior to, during and/or shortly after cardiac surgery or non-cardiac surgery.

In one aspect of this invention the Formula I compound, a prodrug thereof, or a pharmaceutically acceptable salt of said compound or of said prodrug is administered locally.

A preferred dosage is about 0.01 to 100 mg/kg/day of the Formula I compound, a prodrug thereof, or a pharmaceutically acceptable salt of said compound or of said prodrug. An especially preferred dosage is about 0.01 to 50 mg/kg/day of the Formula I compound, a prodrug thereof, or a pharmaceutically acceptable salt of said compound or of said prodrug.

Another aspect of this invention is directed to a method of reducing myocardial tissue damage (e.g., substantially preventing tissue damage, inducing tissue protection) during surgery (e.g., coronary artery bypass grafting (CABG) surgeries, vascular surgeries, percutaneous transluminal coronary angioplasty (PTCA), organ transplantation, or other non-cardiac surgeries) comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method of reducing myocardial tissue damage (e.g., substantially preventing tissue damage, inducing tissue protection) in patients presenting with ongoing cardiac (acute coronary syndromes, e.g. myocardial infarction or unstable angina) or cerebral ischemic events (e.g., stroke) comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a chronic method of reducing myocardial tissue damage (e.g., substantially preventing tissue damage, inducing tissue protection) in a patient with diagnosed coronary heart disease (e.g., previous myocardial infarction or unstable angina) or patients who are at high risk for myocardial infarction (e.g., age>65 and two or more risk factors for coronary heart disease) comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method of preventing ischemic damage comprising the chronic oral administration to a mammal in need of such treatment a therapeutically effective amount of the Formula I compound, a prodrug thereof, or a pharmaceutically acceptable salt of said compound or of said prodrug.

Another aspect of this invention is directed to a method for treating cardiovascular diseases comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating arteriosclerosis comprising administering to a mammal (e.g., a female or male human) a therapeutically effective amount of the Formula I compound, a prodrug thereof, or a pharmaceutically acceptable salt of said compound or of said prodrug Another aspect of this invention is directed to a method for treating hypertension comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating arrhythmia comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating angina pectoris comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating cardiac hypertrophy comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating renal diseases comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating diabetic complications comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating restenosis comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating diseases of cell proliferation comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating cancerous diseases comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating fibrotic diseases comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating glomerular nephrosclerosis comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating pulmonary fibrosis comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating cerebro ischemic disorders comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating myocardial stunning comprising administering to a mammal (e.g., a female or male human) a therapeutically effective amount of a the Formula I compound, a prodrug thereof, or a pharmaceutically acceptable salt of said compound or of said prodrug.

Another aspect of this invention is directed to a method for treating myocardial dysfunction comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating cerebrovascular diseases comprising administering to a mammal (e.g., a female or male human) a therapeutically effective amount of the Formula I compound, a prodrug thereof, or a pharmaceutically acceptable salt of said compound or of said prodrug.

Another aspect of this invention is directed to a method for treating organ hypertrophies or hyperplasias comprising administering to a mammal (e.g., a female or male human) a therapeutically effective amount of the Formula I compound, a prodrug thereof, or a pharmaceutically acceptable salt of said compound or of said prodrug.

This invention is also directed to pharmaceutical compositions which comprise an amount of the Formula I compound, a prodrug thereof, or a pharmaceutically acceptable salt of said compound or of said prodrug and a pharmaceutically acceptable carrier, vehicle or diluent.

This invention is also directed to pharmaceutical compositions for the reduction of tissue damage resulting from ischemia which comprise a therapeutically effective amount of the Formula I compound, a prodrug thereof, or a pharmaceutically acceptable salt of said compound or of said prodrug and a pharmaceutically acceptable carrier, vehicle or diluent.

The term "reduction" is intended to include partial prevention or prevention which, although greater than that which would result from taking no compound or from taking a placebo, is less than 100%, in addition to substantially total prevention.

The term "damage resulting from ischemia" as employed herein refers to conditions directly associated with reduced blood flow to tissue, for example due to a clot or obstruction of blood vessels which supply blood to the subject tissue and which result, inter alia, in lowered oxygen transport to such tissue, impaired tissue performance, tissue dysfunction and/or necrosis. Alternatively, where blood flow or organ perfusion may be quantitatively adequate, the oxygen carrying capacity of the blood or organ perfusion medium may be reduced, e.g., in hypoxic environment, such that oxygen supply to the tissue is lowered, and impaired tissue performance, tissue dysfunction, and/or tissue necrosis ensues.

The term "treating", "treat" or "treatment" as used herein includes preventative (e.g., prophylactic) and palliative treatment.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate (mesylate) and 4-toluene-sulfonate. Since more than one basic moiety exists the expression may include multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The expression "prodrug" refers to compounds that are drug precursors which following administration, release the drug in vivo via some chemical or physiological process (e.g., a prodrug on being brought to the physiological pH or through enzyme action is converted to the desired drug form). Again, there is a proviso that [5-cyclopropyl-1-(quinolin-5-yl)-1H-pyrazole-4-carbonyl]guanidine is not included.

By "pharmaceutically acceptable" it is meant the carrier, diluent, excipients, and/or salt must be compatible with the other ingredients of the formulation, and not deleterious to the recipient thereof.

As used herein, the expressions "reaction-inert solvent" and "inert solvent" refers to a solvent or mixture of solvents which does not interact with starting materials, reagents, intermediates or products in a manner which adversely affects the yield of the desired product.

It will be recognized that the compound of this invention can exist in radiolabelled form, i.e., the compound may contain one or more atoms containing an atomic mass or mass number different from the atomic mass or mass number ordinarily found in nature. Radioisotopes of hydrogen and carbon include $^2H$, $^3H$, and $^{14}C$ respectively. A compound of this invention, which contains those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability. A radiolabelled Formula I compound can generally be prepared by methods well known to those skilled in the art. Conveniently, such radiolabelled compounds can be prepared by carrying out the procedures disclosed in the Schemes and/or in the Examples below by substituting a readily available radiolabelled reagent for a non-radiolabelled reagent.

Other features and advantages will be apparent from the specification and claims which describe the invention.

DETAILED DESCRIPTION OF THE INVENTION

The compound of Formula I is a human metabolite of 5-cyclopropyl-1-(quinolin-5-yl)-1H-pyrazole-4-carbonyl]guanidine. It was identified from samples of human plasma obtained after intravenous administration of 5-cyclopropyl-1-(quinolin-5-yl)-1H-pyrazole-4-carbonyl]guanidine to human subjects. The structure of this compound was independently verified by chemical synthesis. In another aspect of this invention [5-cyclopropyl-1-(2-quinolon-5-yl)-1H-pyrazole-4-carbonyl]guanidine may be prepared by administering [5-cyclopropyl-1-(quinolin-5-yl)-1H-pyrazole-4-carbonyl]guanidine to a human and isolating the desired metabolite from the plasma. Alternatively, the metabolite need not be isolated from the human since it is produced in vivo.

In general the compound of this invention can be made by processes which include processes analogous to those known in the chemical arts, particularly in light of the description contained herein. Certain processes for the manufacture of the compound of this invention are provided as further features of the invention and are illustrated by the following reaction scheme. Other processes are described in the experimental section.

A detailed description of the synthetic aspect of the invention follows:

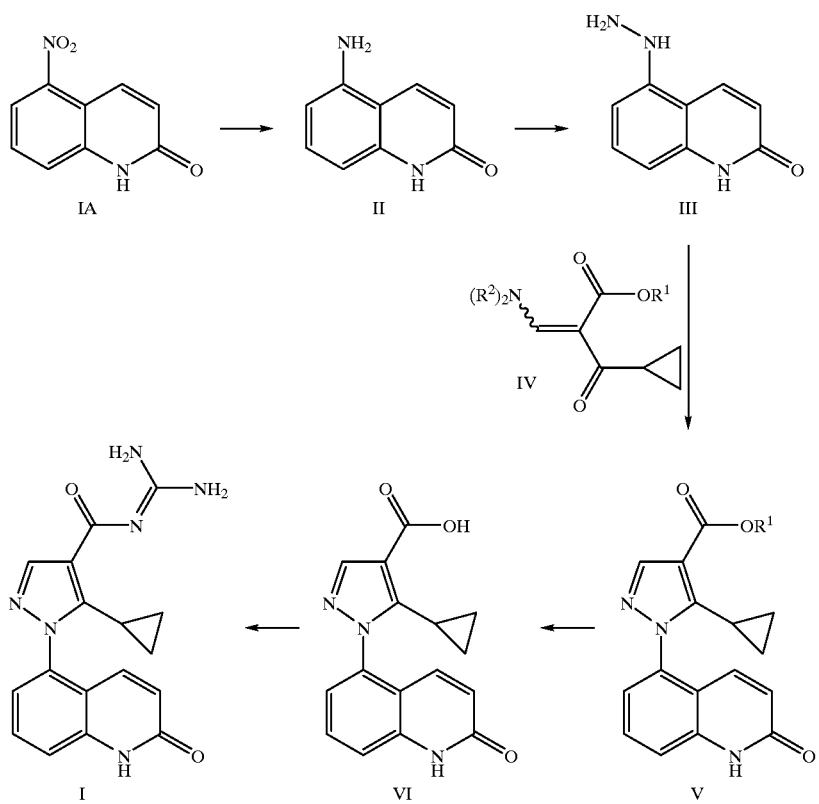

According to the scheme above, the formula IA compound (prepared as described in Capps, J. D.; Hamilton, C. S. *J. Am. Chem. Soc.* 1938, 60, 2104) is dissolved in a protic solvent such as ethanol and treated with an appropriate reducing agent such as stannous chloride dihydrate. The resulting mixture is stirred at a temperature of about 0° C. to about 115° C. for about 30 minutes to about 24 hours. The resulting mixture is cooled to about 23° C. and filtered. The resulting solid material is purified in a suitable way, such as by triturating with hydrochloric acid (for example, 1 M aqueous) at about 100° C. for about 1 hour, cooling to about 23° C. and filtering to provide the formula II compound as its hydrochloride salt. Alternatively, the formula II compound can be isolated from the reaction mixture as the free base by basifying with an inorganic base, and extracting with an appropriate organic solvent. The formula II compound can also be isolated as other salts. Other reduction methods that will perform this reduction are known to those skilled in the art, such as for example catalytic hydrogenation.

The formula II compound is diazotized in hydrochloric acid and water using sodium nitrite at about 0° C. for about 15 minutes to about 2 hours. The resulting diazonium salt solution is reduced with an appropriate reducing agent, such as stannous chloride dihydrate in hydrochloric acid and water at about 0° C. to about 23° C. for about 30 minutes to about 6 hours. The resulting solid is collected by filtration and purified in a suitable manner, such as by trituration with hydrochloric acid (for example, 1 M aqueous) at about 23° C. for about 30 minutes. The compound of formula III is collected by filtration as its hydrochloride salt. Alternatively, the formula III compound can be isolated from the reaction mixture as the free base by basifying, with an inorganic base, and extracting with an appropriate organic solvent. The formula III compound can also be isolated as other salts. Other reducing agents that will perform this transformation are known to those skilled in the art.

The formula IV compound is prepared by methods known to those skilled in the art, such as by the reaction of an N,N-dialkylformamide dialkylacetal, for example, N,N-dimethylformamide dimethylacetal with an ester of 3-cyclopropyl-3-oxopropanoic acid at a temperature of about 23° C. to about 115° C. for about 1 hour to about 4 hours with or without an acid catalyst. The group $R^1$ and $R^2$ are conveniently any alkyl, cycloalkyl, cycloalkylalkyl, or arylalkyl group. Furthermore, the two $R^2$ groups may be tethered together to form a cyclic entity.

The formula IV compound is reacted with the formula III compound in an alcoholic solvent such as ethanol at a temperature of about 23° C. to about 115° C. for about 15 minutes to about 12 hours. When the formula III compound is used as its hydrochloride salt, it is advantageous to carry out the reaction in the presence of an excess of a non-nucleophilic base, such as triethylamine. The formula V compound is collected by filtration. Alternatively, the formula V compound may be isolated by other methods such as concentration followed by addition of water and extraction with a suitable organic solvent. Alternatively, the formula V compound may be prepared using the formula III compound and other compounds in place of the formula IV compound, such as a compound in which the $(R^2)_2N$ group is replaced by a $R^2O$ group.

The formula V compound is hydrolyzed with a base such as sodium or lithium hydroxide in a solvent such as water, and/or methanol, and/or THF conveniently at about 23° C. or at an elevated temperature such as at reflux temperature for about 30 minutes to about 12 hours. The formula VI acid is then isolated by, for example, removing the organic solvents, acidifying and filtering. Alternatively, the formula VI compound can be isolated from the reaction mixture by removing the organic solvents, acidifying and extracting with an appropriate organic solvent.

The Formula VI acid is coupled with guanidine in the presence of a suitable coupling agent. A suitable coupling agent is one which transforms a carboxylic acid into a reactive species which forms an amide linkage on reaction with an amine.

The coupling agent may be a reagent which effects this condensation in a one pot process when mixed together with the carboxylic acid and guanidine. Exemplary coupling reagents are 1-(3-dimethylaminopropyl)-3-ethylcarbodiimide hydrochloride-hydroxybenzotriazole (EDC/HBT), dicyclohexylcarbodiimide (DCC)/hydroxybenzotriazole(HBT), 2-ethoxy-1-ethoxycarbonyl-1, 2-dihydroquinoline (EEDQ), and diethylphosphorylcyanide. The coupling is performed in an inert solvent, preferably an aprotic solvent at a temperature of about −20° C. to about 50° C. for about 1 to about 48 hours, in the presence of excess guanidine as base. Exemplary solvents include acetonitrile, dichloromethane, dimethylsulfoxide, dimethylformamide, chloroform and mixtures thereof.

The coupling agent may also be that agent which converts the carboxylic acid to an activated intermediate which is isolated and/or formed in a first step and allowed to react with guanidine in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate or propanephosphonic anhydride (propanephosphonic acid anhydride, PPA) with a tertiary amine base to form a mixed anhydride of the carboxylic acid, or carbonyldiimidazole to form an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with the intermediate in an appropriate solvent together with an appropriate base. Appropriate solvent/base combinations are for example, dichloromethane, dimethylformamide or acetonitrile or mixtures thereof in the presence of excess guanidine as base. Other appropriate solvent/base combinations include water or a (($C_1$–$C_5$)alcohol) or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature in light of this disclosure. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

In one embodiment, the formula VI acid is activated with excess thionyl chloride at a temperature of about reflux temperature for about 15 minutes to about 3 hours and the excess thionyl chloride is removed by concentration. The resulting acid chloride is combined with excess guanidine hydrochloride and an inorganic base, such as sodium hydroxide in tetrahydrofuran and water. The reaction is stirred conveniently at 23° C. or at an elevated temperature, such as reflux temperature, for about 30 minutes to about 6 hours. The formula I compound is isolated form this reaction mixture in a variety of ways. For example, the reaction mixture is concentrated to remove the THF; the aqueous layer is acidified to pH 9, and the solid is collected by filtration. Alternatively, the formula I compound may be isolated by extraction with an organic solvent. The formula I compound may be transformed to the corresponding hydrochloride salt by treating a solution of it in methanol with hydrogen chloride in ether, and collection of the resulting solid by filtration or concentration. Other salts may be prepared by analogous methods.

Those skilled in the art will recognize that it is also possible to transform the formula V compound directly to the formula I compound by treating the formula V compound with excess guanidine in an inert solvent, such as an alcoholic solvent, for example ethanol, or in the absence of a solvent, at about 60° C. to about 150° C.

Those skilled in the art will recognize that the Formula I compound can exist in several tautomeric forms. All such tautomeric forms are considered as part of this invention. For example, all of the tautomeric forms of the carbonylguanidine moiety of the Formula I compound are included in this invention. All tautomeric forms of the 2-quinolone moiety of the Formula I compound, such as the 2-hydroxyquinoline form, are also included in this invention.

The starting materials and reagents for the above described compounds, are also readily available or can be easily synthesized by those skilled in the art using conventional methods of organic synthesis.

In addition, when the compound of this invention forms metabolites, hydrates or solvates they are also within the scope of the invention.

Some of the compounds (e.g., prodrugs) of this invention are acidic and they form a salt with a pharmaceutically acceptable cation. Most of the compounds of this invention are basic and they form a salt with a pharmaceutically acceptable anion. All such salts, including di- salts are within the scope of this invention and they can be prepared by conventional methods. For example, they can be prepared simply by contacting the acidic and basic entities, in either an aqueous, none-aqueous or partially aqueous medium. The salts are recovered either by filtration, by precipitation with a solvent followed by filtration, by evaporation of the solvent, or, in the case of aqueous solutions, by lyophilization, as appropriate.

The Formula I compound, a prodrug thereof, or a pharmaceutically acceptable salt of said compound or of said prodrug inhibits the sodium/proton (Na+/H+) exchange transport system and hence is useful as a therapeutic or prophylactic agent for diseases caused by the acceleration of the sodium/proton (Na+/H+) exchange transport system, for example, cardiovascular diseases [e.g., arteriosclerosis, hypertension, arrhythmia (e.g., ischemic arrhythmia, arrhythmia due to myocardial infarction, arrhythmia after PTCA or after thrombolysis, etc.), angina pectoris, cardiac hypertrophy, myocardial infarction, heart failure (e.g., congestive heart failure, acute heart failure, cardiac hypertrophy, etc.), restenosis after PTCA, shock (e.g. hemorrhagic shock, endotoxin shock, etc.)], renal diseases (e.g., diabetes mellitus, diabetic nephropathy, ischemic acute renal failure, etc.) organ disorders associated with ischemia or ischemic reperfusion [(e.g., heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g., ischemic stroke, hemorrhagic stroke, etc.), cerebro ischemic disorders (e.g., disorders associated with cerebral infarction, disorders caused after cerebral apoplexy as sequelae, or cerebral edema). The Formula I compound, a prodrug thereof, or a pharmaceutically acceptable salt of said compound or of said prodrug can also be used as an agent for myocardial protection during coronary artery bypass grafting (CABG) surgeries, vascular surgeries, percutaneous transluminal coronary angioplasty (PTCA), organ transplantation, or non-cardiac surgeries.

Preferably, the Formula I compound, a prodrug thereof, or a pharmaceutically acceptable salt of said compound or of said prodrug can be used as agents for myocardial protection before, during, or after coronary artery bypass grafting (CABG) surgeries, vascular surgeries, percutaneous transluminal coronary angioplasty (PTCA), organ transplantation, or non-cardiac surgeries.

Preferably, the Formula I compound, a prodrug thereof, or a pharmaceutically acceptable salt of said compound or of said prodrug can be used as agents for myocardial protection in patients presenting with ongoing cardiac (acute coronary syndromes, e.g., myocardial infarction or unstable angina) or cerebral ischemic events (e.g., stroke).

Preferably, the Formula I compound, a prodrug thereof, or a pharmaceutically acceptable salt of said compound or of said prodrug can be used as agents for chronic myocardial protection in patients with diagnosed coronary heart disease (e.g., previous myocardial infarction or unstable angina) or patients who are at high risk for myocardial infarction (e.g., age greater than 65 and two or more risk factors for coronary heart disease).

In addition to this, the Formula I compound, a prodrug thereof, or a pharmaceutically acceptable salt of said compound or of said prodrug are notable for their strong inhibitory effect on the proliferation of cells, for example the proliferation of fibroblast cells and the proliferation of the smooth muscle cells of the blood vessels. For this reason, the Formula I compound, a prodrug thereof, or a pharmaceutically acceptable salt of said compound or of said prodrug are valuable therapeutic agents for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, glomerular nephrosclerosis, organ hypertrophies or hyperplasias, in particular hyperplasia or hypertrophy of the prostate, pulmonary fibrosis, diabetic complications or recurrent stricture after PTCA, or diseases caused by endothelial cell injury.

The utility of the Formula I compound, a prodrug thereof, or a pharmaceutically acceptable salt of said compound or of said prodrug as medical agents in the treatment of diseases, such as are detailed herein in mammals (e.g., humans) for example, myocardial protection during surgery or mycardial protection in patients presenting with ongoing cardiac or cerebral ischemic events or chronic cardioprotection in patients with diagnosed coronary heart disease, is demonstrated by the activity of the Formula I compound, or a pharmaceutically acceptable salt of said compound in conventional in vitro and other preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430-H2440 (1994); the NMR assay in Kolke et al., J. Thorac. Cardiovasc. Surg. 112:765–775 (1996)]. Such assays also provide a means whereby the activities of the Formula I compound, or a pharmaceutically acceptable salt of said compound or of said prodrug can be compared with the activities of other known compounds. The results of these comparisons are useful for determining dosage levels in mammals, including humans, for the treatment of such diseases.

Measurement of Human NHE-1 Inhibitory Activity

Methodologies for measurement of human NHE-1 activity and inhibitor potency are based on those published by Watson et al., Am. J. Physiol., 24:G229–G238, 1991), where NHE-mediated recovery of intracellular pH is measured following intracellular acidification. Thus, fibroblasts stably expressing human NHE-1 (Counillon, L. et al., Mol. Pharmacol., 44:1041–1045 (1993) are plated onto collagen coated 96 well plates (50,000/well) and grown to confluence in growth media (DMEM high glucose, 10% fetal bovine serum, 50 u/ml penicillin and streptomycin). Confluent plates are incubated for 30 min at 37° C. with the pH sensitive fluorescent probe BCECF (5 $\mu$M; Molecular Probes, Eugene, Oreg.). BCECF loaded cells are incubated for 30 min at 37° C. in acid loading media (70 mM choline chloride, 50 mM $NHCl_4$, 5 mM KCl, 1 mM $MgCl_2$, 1.8 mM $CaCl_2$, 5 mM glucose, 10 mM HEPES, pH 7.5), and then placed in a Fluorescent Imaging Plate Reader (Molecular Devices, CA). BCECF fluorescence is monitored using excitation and emission wavelengths of 485 nM and 525 nM, respectively. Intracellular acidification is initiated via rapid replacement of acid loading media with recovery media (120 mM NaCl, 5 mM KCl, 1 mM $MgCl_2$, 1.8 mM $CaCl_2$, 5 mM glucose, 10 mM HEPES, pH 7.5)±test compound, and NHE-mediated recovery of intracellular pH is monitored as the subsequent time-dependent increase BCECF fluorescence. The potency of human NHE-1 inhibitors is calculated as the concentration that reduces recovery of intracellular pH by 50% ($IC_{50}$). Under these conditions reference NHE inhibitors amiloride and HOE-642 had $IC_{50}$ values for human NHE-1 of 50 $\mu$M and 0.5 $\mu$M, respectively. The compound of Formula I demonstrated an $IC_{50}$ value of 200 nM in the above assay.

It has been reported that brief periods of myocardial ischemia followed by coronary artery reperfusion protects the heart from subsequent severe myocardial ischemia (Murry et al., Circulation 74:1124–1136, 1986). This phenomenon is known as ischemic preconditioning.

The therapeutic effects of the compounds of this invention in preventing heart tissue damage resulting from an ischemic insult can be demonstrated in vitro along lines presented in Liu et al. (Cardiovasc. Res., 28:1057–1061, 1994), as described specifically herein. Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994). The in vitro test described below demonstrates that an active test compound can also pharmacologically induce cardioprotection, i.e., reduce myocardial infarct size, when administered to a rabbit isolated heart. The effects of the test compound are compared to ischemic preconditioning and the A1/A3 adenosine agonist, APNEA (N$^6$-[2-(4-aminophenyl)ethyl] adenosine), that has been shown to pharmacologically induce cardioprotection in the rabbit isolated heart (Liu et al., Cardiovasc. Res., 28:1057–1061, 1994). The exact methodology is described below.

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a prominent branch of the left coronary artery, approximately ⅔ of the distance towards the apex of the heart. The heart is removed from the chest and rapidly (<30 sec) mounted on a Langendorff apparatus. The heart is retrogradely perfused in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure$\leq$10 mmHg. Total coronary flow is also continuously monitored using an in-line flow probe and normalized for heart weight.

The heart is allowed to equilibrate for 30 min, over which time the heart must show stable left ventricular pressures within the parameters outlined above. If the heart rate falls below 180 bpm at any time prior to the 30 min period of regional ischemia, the heart is paced at about 200 bpm for the remainder of the experiment. ischemic preconditioning is induced by total cessation of cardiac perfusion (global ischemia) for 5 min, followed by reperfusion for 10 min. The regional ischemia is provided by tightening the snare around the coronary artery branch. Following the 30 min regional ischemia, the snare is released and the heart reperfused for an additional 120 min.

Pharmacological cardioprotection is induced by infusing the test compound at predetermined concentrations, starting 30 min prior to the 30 min regional ischemia, and continuing until the end of the 120 min reperfusion period. Hearts which receive test compound do not undergo the period of ischemic preconditioning. The reference compound, APNEA (500 nM) is perfused through hearts (which do not receive the test compound) for a 5 min period which ends 10 min before the 30 min regional ischemia.

At the end of the 120 min reperfusion period, the coronary artery snare is tightened, and a 0.5% suspension of fluorescent zinc cadmium sulfate particles (1–10 $\mu$M) Duke Scientific Corp.(Palo Alto, Calif.) is perfused through the heart; this stains all of the myocardium, except that area-at-risk for infarct development (area-at-risk). The heart is removed from the Langendorff apparatus, blotted dry, wrapped in aluminum foil and stored overnight at −20° C. The next day, the heart is sliced into 2 mm transverse sections from the apex to the top of the ventricles. The slices are stained with 1% triphenyl tetrazolium chloride (TTC) in phosphate-buffered saline for 20 min at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for differences in the area-at-risk between hearts, the data is expressed as the ratio of infarct area vs. area-at-risk (% IA/AAR). All data are expressed as mean±SE and compared statistically using a Mann-Whitney non-parametric test with a Bonferroni correction for multiple comparisons. Significance is considered as p<0.05.

The results from the above in vitro test can be used to demonstrate that compounds of this invention induce significant cardioprotection relative to the control group.

Administration of the Formula I compound, a prodrug thereof, or a pharmaceutically acceptable salt of said compound or of said prodrug can be via any method which delivers the Formula I compound, a prodrug thereof, or a pharmaceutically acceptable salt of said compound or of said prodrug preferentially to the desired tissue (e.g., liver and/or cardiac tissues). These methods include oral routes, parenteral, intraduodenal routes, etc. Generally, the Formula I compound, a prodrug thereof, or a pharmaceutically acceptable salt of said compound or of said prodrug is administered in single (e.g., once daily) or multiple doses or via constant infusion in, for example, an isotonic saline solution.

The Formula I compound, a prodrug thereof, or a pharmaceutically acceptable salt of said compound or of said prodrug is useful, for example, in reducing or minimizing damage effected directly to any tissue that may be susceptible to ischemia/reperfusion injury (e.g., heart, brain, lung, kidney, liver, gut, skeletal muscle, retina), through for example mediation by NHE-1, as the result of an ischemic event (e.g., myocardial infarction). The active compound is therefore usefully employed prophylactically to prevent, (i.e., prospectively or prophylactically) to blunt or stem, tissue damage (e.g., myocardial tissue) in patients who are at risk for ischemia (e.g., myocardial ischemia).

Generally, the Formula I compound, a prodrug thereof, or a pharmaceutically acceptable salt of said compound or of said prodrug of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

The amount and timing of the Formula I compound, a prodrug thereof, or a pharmaceutically acceptable salt of said compound or of said prodrug administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

Typically an amount of the Formula I compound, a prodrug thereof, or a pharmaceutically acceptable salt of said compound or of said prodrug is used that is effective for ischemic protection. A preferred dosage is about 0.01 to 100 mg/kg/day of the Formula I compound, a prodrug thereof, or a pharmaceutically acceptable salt of said compound or of said prodrug of this invention. An especially preferred dosage is about 0.01 to 50 mg/kg/day of the Formula I compound, a prodrug thereof, or a pharmaceutically acceptable salt of said compound or of said prodrug of this invention.

In one mode of administration the Formula I compound, a prodrug thereof, or a pharmaceutically acceptable salt of said compound or of said prodrug may be administered just prior to cardiac surgery (e.g., within twenty-four hours before surgery), during or subsequent to cardiac surgery (e.g., within twenty-four hours after surgery) where there is risk of myocardial ischemia. In an especially preferred mode an infusion is administered with a loading dose of about 1 mg to about 300 mg for about one minute to about one hour prior to surgery followed by a constant infusion of about 1 mg/kg/day to about 100 mg/kg/day for the remaining presurgery, surgery and post surgery periods, including for example about 2 to about 7 days post surgical treatment. The compound of this invention may also be administered in a chronic daily mode.

The Formula I compound, a prodrug thereof, or a pharmaceutically acceptable salt of said compound or of said prodrug is generally administered in the form of a pharmaceutical composition comprising the Formula I compound, a prodrug thereof, or a pharmaceutically acceptable salt of said compound or of said prodrug together with a pharmaceutically acceptable vehicle, carrier or diluent. Thus, the Formula I compound, a prodrug thereof, or a pharmaceutically acceptable salt of said compound or of said prodrug can be administered in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain for example 0.0001%–95% of the Formula I compound, a prodrug thereof, or a pharmaceutically acceptable salt of said compound or of said prodrug. In any event, the composition or formulation to be administered will contain an amount effective to treat the disease/condition of the subject being treated.

The Formula I compound, a prodrug thereof, or a pharmaceutically acceptable salt of said compound or of said prodrug generally will be administered in a convenient formulation. The following formulation examples are illustrative only and are not intended to limit the scope of the present invention.

In the formulations which follow, "active ingredient" means the Formula I compound, a prodrug thereof, or a pharmaceutically acceptable salt of said compound or of said prodrug.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly.

The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 mL) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 25 mg |
| Isotonic saline | 1,000 mL |

The solution of the above ingredients is intravenously administered to a patient.

General Experimental Procedures 300 and 400 MHz $^1$H NMR spectra were recorded on a Varian Unity+300 or 400 spectrometer (Varian Co., Palo Alto, Calif.) equipped with two RF channels, indirect detection, and pulsed-field gradients (Z-axis only). Spectra were generally acquired near room temperature (21° C.), and standard auto-lock and auto-shim routines were employed for shimming samples. Chemical shifts are expressed in parts per million downfield from trimethylsilane. The peak shapes are denoted as follows: s, singlet; d, doublet; t, triplet, q, quartet; m, multiplet; bs, broad singlet. Resonances designated as exchangeable did not appear in a separate NMR experiment where the sample was shaken with several drops of $D_2O$ in the same solvent. Atmospheric pressure chemical ionization mass spectra (APCIMS) were obtained on a Fisons Platform II or a Micromass ZMD spectrometer (Microsmass, Manchester, U.K.). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and M is based on $^{35}Cl$ and $^{79}Br$. In some cases only representative $^1$H NMR and APCIMS peaks are given.

Column chromatography was performed with either Baker Silica Gel (40 μm) (J. T. Baker, Phillipsburg, N.J.) or Silica Gel 60 (EM Sciences, Gibbstown, N.J.) in glass columns or in Flash 12, 40 or 75 (Biotage) (Charlottesville, Va.) columns under low nitrogen pressure. Radial Chromatography was performed using a Chromatotron, (Harrison Research, Palo Alto, Calif.) Unless otherwise specified, reagents were used as obtained from commercial sources. Dimethylformamide, 2-propanol, methanol, dimethylsulfoxide, 1,2-dichloroethane, tetrahydrofuran, toluene, dichloromethane and other reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated in vacuo" and "removed in vacuo" refer to removal of solvent at reduced pressure on a rotary evaporator with a bath temperature of less than 90° C. Reactions conducted at "0–20° C." or "0–25° C." were conducted with initial cooling of the vessel in an insulated ice bath which was allowed to warm to room temperature over several hours. The abbreviation "min" and "h" stand for "minutes" and "hours" respectively.

EXAMPLE 1

5-Amino-2-guinolone Hydrochloride

A solution of the 5-nitro-2-quinolone (12.37 g, 65 mmol) (prepared as described in Capps, J. D.; Hamilton, C. S. *J. Am. Chem. Soc.* 1938, 60, 2104) in EtOH (176 mL) under a nitrogen atmosphere was treated with $SnCl_2.2H_2O$ (73.4 g, 325 mmol). The heterogeneous reaction mixture was allowed to stir at 23° C. for 2 hours and heated at reflux for 2 hours. The resulting heterogeneous mixture was cooled to 23° C. and filtered. The solid material was triturated in HCl (1 M aqueous, 78 mL, 78 mmol) at reflux for 1 hour, cooled to 23° C., and filtered to afford 10.08 g of the desired product (78% yield).

$^1$H NMR (400 MHz, DMSO-$d_6$) δ 6.42 (d, J=10, 1H), 6.71 (d, J=7.6, 1H), 6.81 (d, J=8, 1H), 7.27 (d, J=8, 1H), 8.04 (d, J=10, 1H), 11.71 (bs, 1H).

APCIMS 161 [M+1]$^+$

EXAMPLE 2

5-Hydrazino-2-guinolone Hydrochloride

A solution of 5-amino-2-quinolone hydrochloride (10.08 g, 51.2 mmol) in HCl (concentrated, 42.7 mL) and $H_2O$ (18.2 mL) at 0° C. was treated dropwise with a solution of NaNO$_2$ (3.53 g, 51.2 mmol) in H$_2$O (26.4 mL) while maintaining the temperature below 5° C. The resulting red suspension was allowed to stir at 0° C. for 1 hour.

In a separate three neck round bottom flask equipped with a mechanical stirrer, a slurry of SnCl$_2$.2H$_2$O (25.41 g, 112.6 mmol) in HCl (concentrated, 34.2 mL) and H$_2$O (93.9 mL) was cooled to 0° C. The suspension was treated dropwise with the red diazonium salt suspension prepared above, while maintaining the temperature below 5° C. The reaction mixture was warmed to 23° C. and allowed to stir for 3 hours. The resulting suspension was filtered. The collected solid was triturated with HCl (1 M aqueous, 61.4 mL, 61.4 mmol) at 23° C. for 30 minutes. The solid was collected by filtration to afford 7.88 g of the desired product (73% yield).

$^1$H NMR (400 MHz, DMSO-d$_6$) δ 6.43 (d, J=10, 1H), 6.63 (d, J=8, 1H), 6.88 (d, J=8, 1H), 7.38 (t, J=8, 1H), 7.98 (d, J=10, 1H), 8.97 (bs, 1H), 10.40 (bs, 1H), 11.77 (bs, 1H).

APCIMS 176 [M+1]$^+$

EXAMPLE 3

Methyl 5-cyclopropyl-1-(2-guinolon-5-yl)-1H-pyrazole-4-carboxylate

A solution of methyl 3-cyclopropyl-2-(dimethylaminomethylene)-3-oxopropanoate (7.85 g, 39.8 mmol) in EtOH (257 mL) was treated under a nitrogen atmosphere with triethylamine (7.77 mL, 55.8 mmol), followed by 5-hydrazino-2-quinolone hydrochloride (7.88 g, 37.2 mmol). The resulting heterogeneous reaction mixture was heated at reflux for 4 hours and cooled to 23° C. A pale yellow solid precipitated out and was collected by filtration to afford 5.06 g of the desired product (44% yield).

$^1$H NMR (300 MHz, DMSO-d$_6$) δ 0.59–0.73 (m, 4H), 1.87 (m, 1H), 3.79 (s, 1H), 6.54 (d, J=10, 1H), 7.17 (d, J=10, 1H), 7.34 (d, J=7.5, 1H), 7.49 (d, J=8, 1H), 7.66 (t, J=8, 1H), 8.08 (s, 1H), 12.10 (bs, 1H).

APCIMS 310 [M+1]$^+$

EXAMPLE 4

5-Cyclopropyl-1-(2-guinolon-5-yl)-1H-pyrazole-4-carboxylic Acid

A slurry of methyl 5-cyclopropyl-1-(2-quinolon-5-yl)-1H-pyrazole-4-carboxylate (5.06 g, 16.4 mmol) in THF (81.8 mL) and MeOH (40.9 mL) was treated with LiOH (1 M aqueous, 81.8 mL, 81.8 mmol) and heated at reflux for 2.5 hours. The resulting heterogeneous mixture was cooled to 23° C. The MeOH and THF were removed in vacuo. The resulting slurry was cooled to 0° C. and acidified to pH 3–4 using HCl (concentrated). The mixture was filtered. The solid was dried to afford 4.94 g of desired product (100% yield).

$^1$H NMR (400 MHz, DMSO-d6) δ 0.58 (d, J=4.4, 2H), 0.64 (d, J=8, 2H), 1.82 (m, 1H), 6.50 (d, J=10, 1H), 7.12 (d, J=10, 1H), 7.27 (d, J=7.6, 1H), 7.44 (d, J=8.4, 1H), 7.60 (t, J=8, 1H), 7.97 (s, 1H), 12.03 (bs, 1H), 12.38 (bs, 1H).

APCIMS 296 [M+1]$^+$

EXAMPLE 5

[5-Cyclopropyl-1-(2-guinolon-5-yl)-1H-pyrazole-4-carbonyl]quanidine Hydrochloride A solution of 5-cyclopropyl-1-(2-quinolon-5-yl)-1H-pyrazole-4-carboxylic acid (13.27 g, 45.0 mmol) in SOCl$_2$ (60 mL) was heated at reflux for 1 hour. The excess SOCl$_2$ was removed in vacuo. The residue was treated with dry toluene and concentrated in vacuo. A solution of the solid residue in THF (50 mL) was treated with a solution of guanidine hydrochloride (15.47 g, 162 mmol) in NaOH (2 M aqueous, 162 mL, 324 mmol) under a nitrogen atmosphere. The resulting mixture was stirred at 23° C. for 2 hours. The reaction mixture was then concentrated in vacuo to remove the THF. The aqueous layer was cooled to 0° C. and acidified to pH 9. A pale yellow solid precipitated and was collected to afford 11.41 g of the free base of the desired compound. A solution of the solid in MeOH (700 mL) was treated with HCl (1 M in ether, 84.9 mL, 84.9 mmol). The solvent volume was reduced in vacuo. The resulting pale brown precipitate was collected to afford 8.49 g (51% yield). (Additional product as the free base may be obtained by extraction of the aqueous layer using EtOAc-THF (1:1)).

$^1$H NMR (400 MHz, DMSO-d$_6$) δ 0.51 (m, 2H), 0.70 (dd, J=2, 8.4, 2H), 1.92 (m, 1H), 6.53 (dd, J=1.6, 10, 1H), 7.17 (d, J=10, 1H), 7.32 (d, J=7, 1H), 7.48 (d, J=8.4, 1H), 7.64 (t, J=8.2, 1H), 8.34 (bs, 2H), 8.60 (bs, 3H), 11.64 (s, 1H), 12,10 (s, 1H).

APCIMS 337 [M+1]$^+$

EXAMPLE 6

Identification of [5-cyclopropyl-1-(2-guinolon-5-yl)-1H-pyrazole-4-carbonyl]guanidine in Human Plasma Samples by Liquid Chromatography (LC)/mass Spectroscopy (MS)/MS and LC/NMR Human subjects were dosed intravenously with 5-cyclopropyl-1-(quinolin-5-yl)-1H-pyrazole-4-carbonyl] guanidine monohydrochloride monohydrate. Human plasma samples were pooled together and proteins were precipitated by twice volume of acetonitrile. After centrifugation, the supernatant was concentrated in a water bath with N$_2$ at 40° C.

An aliquot (100 μL or 50 μL) of the concentrated sample was injected onto an LC/MS/MS instrument equipped with a Zorbax Rx-C8 4.6×150 mm column, analyzed on PE Sciex API 2000 or Finnigan LCQ mass spectrometer and monitored by UV detector at 254 nm. The eluent from the column was split so that 5% of eluent was diverted to the mass spectrometer and the rest was passed to UV detector. The analyses were performed using a mobile phase flow rate of 1 ml/minute, where the mobile phase consisted of 5 mM ammonium formate (pH 3.0) as solvent A and acetonitrile as solvent B. A gradient included 5/95 to 40/60 of B/A over a 20 minute period after an initial hold for 3 minutes. Under these LC conditions a metabolite was detected at a retention time of 11.8 minutes ([5-cyclopropyl-1-(quinolin-5-yl)-1H-pyrazole-4-carbonyl]guanidine was detected at 13.7 minutes). The 16 mass units difference between 5-cyclopropyl-1-(quinolin-5-yl)-1H-pyrazole-4-carbonyl] guanidine (m/z 321) and metabolite (m/z 337) in human plasma suggested that it is formed through oxidation. LC/MS/MS product ion spectrum of protonated metabolite at m/z 337 ([M+H]$^+$) showed fragment ions at m/z 278, 260, 250, 236, 223 and 208.

The salts were removed from the above concentrated sample by solid phase extraction. The sample was concentrated to contain approximately 5–10 μg of the metabolite. 50 μL of this sample was injected onto an LC/NMR instrument equipped with a Zorbax Rx-C8 4.6×150 mm column, analyzed on a Bruker 500 MHz NMR spectrometer and monitored by UV detector at 235 nm. The analyses were performed using a mobile phase flow rate of 1 ml/minute, where the mobile phase consisted of 15 mM deuterated aqueous formic acid adjusted to pH 3.3 with deuterated ammonium hydroxide in D$_2$O as solvent C and acetonitrile-d$_3$ as solvent D. A gradient included 5/95 to 20/80 of D/C over a 17 minute period after an initial hold for 3 minutes. The desired metabolite was captured in the NMR probe using the stop flow technique on the peak at 13.6 minutes. Proton NMR spectra and COSY spectra of the human metabolite contained two doublets (6.64 and 7.41 ppm) which were coupled to each other but not to any other peaks. The absence of the downfield peak at 8.92 ppm that is present in [5-cyclopropyl-1-(quinolin-5-yl)-1H-pyrazole-4-carbonyl]guanidine suggested that the 2-position on the quinoline ring was the site of oxidation. On the basis of this data the structure of the metabolite was assigned as [5-cyclopropyl-1-(2-quinolon-5-yl)-1H-pyrazole-4-carbonyl]guanidine. Comparison of the $^1$H LC/NMR spectrum of the metabolite to that of a synthetic standard of [5-cyclopropyl-1-(2-quinolon-5-yl)-1H-pyrazole-4-carbonyl]guanidine hydrochloride, prepared as described in Example 5, confirmed the structural assignment.

What is claimed is:

1. An isolated compound having the Formula I

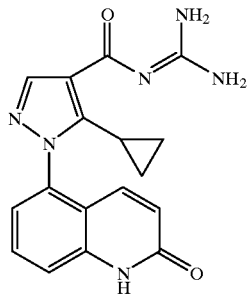

Formula I or a pharmaceutically acceptable salt of said compound [5-cyclopropyl-1-(quinolin-5-yl)-1H-pyrazole-4-carbonyl]guanidine.

2. Isolated [5-Cyclopropyl-1-(2-quinolon-5-yl)-1H-pyrazole-4-carbonyl]guanidine.

3. A method of reducing tissue damage resulting from ischemia or hypoxia comprising administering to a mammal in need of such treatment a therapeutically effective amount of a compound of claim 1, or a pharmaceutically acceptable salt of said compound.

4. A method as recited in claim 3 wherein the tissue is cardiac, brain, liver, kidney, lung, gut, skeletal muscle, spleen, pancreas, nerve, spinal cord, retina tissue, the vasculature, or intestinal tissue.

5. A method as recited in claim 3 wherein the amount of the compound of claim 1, or a pharmaceutically acceptable salt of said compound is about 0.01 mg/kg/day to about 50 mg/kg/day.

6. A method as recited in claim 5 wherein the mammal is a female or male human.

7. A method as recited in claim 6 wherein said tissue is heart tissue.

8. A method as recited in claim 6 wherein said tissue is brain tissue.

9. A method as recited in claim 6 wherein said tissue is liver tissue.

10. A method as recited in claim 6 wherein said tissue is kidney tissue.

11. A method as recited in claim 6 wherein said tissue is lung tissue.

12. A method as recited in claim 6 wherein said tissue is gut tissue.

13. A method as recited in claim 6 wherein said tissue is skeletal muscle tissue.

14. A method as recited in claim 6 wherein said tissue is spleen tissue.

15. A method as recited in claim 6 wherein said tissue is pancreas tissue.

16. A method as recited in claim 6 wherein said tissue is retina tissue.

17. A method as recited in claim 6 wherein the compound is administered prophylactically.

18. A method as recited in claim 6 wherein the compound is administered prior to surgery.

19. A method as recited in claim 6 wherein the compound is administered prior to cardiac surgery.

20. A method as recited in claim 6 wherein the compound is administered during surgery.

21. A method as recited in claim 6 wherein the compound is administered during cardiac surgery.

22. A method as recited in claim 6 wherein the compound is administered within twenty-four hours after surgery.

23. A method as recited in claim 6 wherein the compound is administered within twenty four hours after cardiac surgery.

24. A method as recited in claim 6 wherein the tissue damage resulting from ischemia is ischemic damage and is incurred during organ transplantation.

25. A method as recited in claim 6 wherein the compound is administered to prevent perioperative myocardial ischemic injury.

26. A pharmaceutical composition which comprises a compound of claim 1, or a pharmaceutically acceptable salt of said compound and a pharmaceutically acceptable carrier, vehicle or diluent.

27. A pharmaceutical composition for the reduction of tissue damage resulting from ischemia or hypoxia which comprises a therapeutically effective amount of the compound of claim 1, or a pharmaceutically acceptable salt of said compound and a pharmaceutically acceptable carrier, vehicle or diluent.

28. A method as recited in claim 6 wherein the compound is administered prior to, during and after surgery.

29. A method as recited in claim 6 wherein the compound is administered prior to, during and after cardiac surgery.

30. Substantially pure [5-cyclopropyl-1-(2-quinolon-5-yl)-1H-pyrazole-4-carbonyl]guanidine, or a pharmaceutically acceptable salt of said compound.

* * * * *